United States Patent [19]

Sutter

[11] Patent Number: 5,037,847

[45] Date of Patent: Aug. 6, 1991

[54] PYRROLE ACRYLIC ACID ESTERS AS FUNGICIDES

[75] Inventor: Marius Sutter, Basel, Switzerland

[73] Assignee: Ciba-Geigy Corporation, Ardsley, N.Y.

[21] Appl. No.: 489,413

[22] Filed: Mar. 6, 1990

[30] Foreign Application Priority Data

Mar. 8, 1989 [CH] Switzerland .......................... 865/89

[51] Int. Cl.$^5$ .................... A61K 31/40; A01N 47/40; C07D 207/34; C07D 405/10
[52] U.S. Cl. ................................. 514/427; 426/532; 548/461; 548/526; 514/422
[58] Field of Search ................ 548/561, 526; 514/427, 514/422; 426/532

[56] References Cited

U.S. PATENT DOCUMENTS

| 4,229,465 | 10/1980 | Ohkuma et al. | 424/274 |
| 4,705,801 | 11/1987 | Martin | 548/561 |
| 4,868,202 | 9/1989 | Martin et al. | 514/427 |
| 4,883,807 | 11/1989 | Clough | 548/561 |

FOREIGN PATENT DOCUMENTS 0206523 12/1986 European Pat. Off. .

Primary Examiner—Mark L. Berch

Attorney, Agent, or Firm—George R. Dohmann; Edward McC. Roberts

[57] ABSTRACT

Novel 3-aryl-4-cyanopyrrole derivatives of the general formula

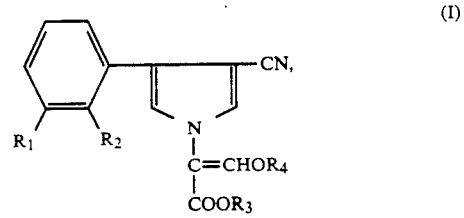

wherein
$R_1$ and $R_2$ are each independently of the other unsubstituted or halogen-substituted alkyl, halogen, nitro or hydrogen, or $R_1$ and $R_2$, when taken together, are —OCF$_2$O,
$R_3$ is alkyl, cycloalkyl or benzyl, and
$R_4$ is hydrogen or an alkali metal or alkaline earth metal.

The novel compounds are used for controlling harmful microorganisms, in particular phytopathogenic fungi. They can be used together with suitable formulation assistants as compositions, and are also suitable for preventing infestation of cultivated plants by harmful microorganisms.

11 Claims, No Drawings

PYRROLE ACRYLIC ACID ESTERS AS FUNGICIDES

The present invention relates to novel substituted 3-aryl-4-cyanopyrrole derivatives, to the preparation thereof, and also to microbicidal compositions which contain at least one of said compounds. The invention further relates to the preparation of these compositions and to the use of the novel compounds and compositions for controlling harmful microorganisms, in particular phytopathogenic fungi.

The compounds of this invention have the general formula I

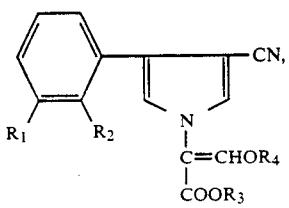

wherein
$R_1$ and $R_2$ are each independently of the other unsubstituted or halogen-substituted $C_1$-$C_8$alkyl, and are also halogen, nitro or hydrogen, or $R_1$ and $R_2$, when taken together, are —$OCF_2O$—,
$R_3$ is $C_1$-$C_8$alkyl, cycloalkyl or benzyl, and
$R_4$ is hydrogen or an alkali metal or alkaline earth metal.

On account of their pronounced microbicidal activity, those compounds of formula I are preferred in which $R_4$ is hydrogen. Among these compounds, those compounds are especially preferred in which $R_1$ and $R_2$ are each independently of the other unsubstituted or halogen-substituted $C_1$-$C_8$alkyl, halogen, nitro or hydrogen, or $R_1$ and $R_2$, when taken together, are —$OCF_2O$—, and $R_3$ is $C_1$-$C_8$alkyl or benzyl.

Depending on the indicated number of carbon atoms, alkyl will be understood as meaning typically the following groups: methyl, ethyl, propyl, butyl, pentyl, hexyl, octyl and the like, and the isomers thereof such as isopropyl, sec-butyl, isobutyl, tert-butyl, isopentyl, isohexyl, and the like. Haloalkyl is a monosubstituted to perhalogenated alkyl substituent such as $CH_2Cl$, $CHCl_2$, $CCl_3$, $CH_2Br$, $CHBr_2$, $CBr_3$, $CH_2F$, $CHF_2$, $CF_3$, $CCl_2F$, $CCl_2$—$CHCl_2$, $CH_2CH_2F$, $CI_3$ and the like. Throughout this specification, halogen will be understood as meaning fluoro, chloro, bromo or iodo, preferably fluoro, chloro or bromo.

Cycloalkyl will be understood as meaning cyclopropyl, cyclobutyl, cyclopentyl, cyclohexyl or cycloheptyl.

Among the above mentioned compounds, those compounds are particularly preferred in which $R_1$ and $R_2$ are each independently of the other methyl, trifluoromethyl, chloro, bromo or hydrogen, or or $R_1$ and $R_2$, when taken together, are —$OCF_2O$—, and $R_3$ is methyl, ethyl, n-hexyl or benzyl.

Among this group of compounds, those compounds are especially preferred in which $R_3$ is methyl or ethyl.

Particularly preferred individual compounds on account of their excellent fungicidal action are methyl 2-[3-(2,2-difluorobenzodioxol-4-yl)-4-cyanopyrrol-1-yl]-3-hydroxyacrylate and methyl 2-[3-(2,3-dichlorophenyl)-4-cyanopyrrol-1-yl]-3-hydroxyacrylate.

Under normal conditions the compounds of formula I are stable oils, resins or mainly crystalline solids which have extremely valuable microbicidal properties. They can be used, for example, in agriculture or related fields for the preventive or curative control of phytopathogenic microorganisms. The compounds of formula I have very good fungicidal activity in a wide range of concentrations, and their application poses no problems.

The compounds of formula I are prepared by reacting a compound of formula II, in the presence of a base, with a compound of formula III or with another formylating reagent

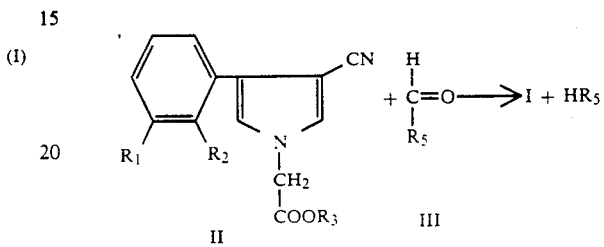

in which formulae II and III above the substituents $R_1$ to $R_3$ are as defined for formula I and $R_5$ is an alkoxy or dialkylamino group.

The reaction product obtained by this process can be in the form of an enolate salt, in which case $R_4$ in formula I is an alkali metal or alkaline earth metal, or of the free enol, in which case $R_4$ is hydrogen. The enols can be liberated from the enolate salts e.g. by the addition of acid, for example aqueous hydrochloric acid, and isolated.

The reaction is carried out in the temperature range from —30° to 150° C., preferably from 20° to 80° C., in a suitable solvent. Preferred solvents are tetrahydrofuran, ethers and acetonitrile. Further preferred solvents are those which simultaneously act as formylating agent, for example the esters of formic acid.

Suitable bases are typically hydrides, hydroxides and alcoholates of alkali metals or alkaline earth metals, for example NaH, KOH and NaOR₃.

Aside from the compounds of formula III, suitable formylating agents are known from the literature (G.A. Olah et al., Chemical Reviews, 87, 67 (1987). The preparation of the intermediates of formula II is effected by methods analogous to known condensation reactions by reacting the 3-aryl-4-cyanopyrrole (IV) with a haloacetate such as methyl bromoacetate (V) in the presence of a base, for example $K_2CO_3$:

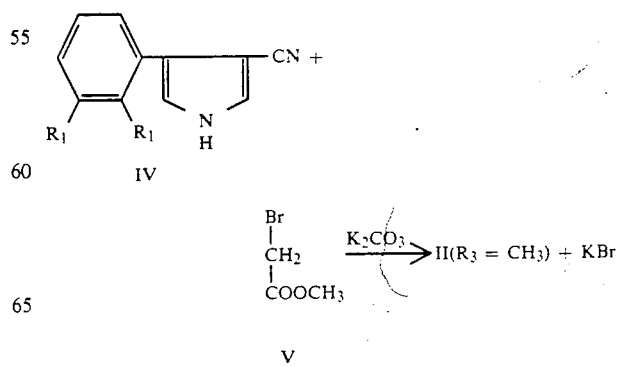

Microbicides which are structurally similar to the compounds of formula I, and which carry a propionic acid ester group at the nitrogen atom of the pyrrole, are disclosed in European patent application 0 182 737. Compared with these known N-substituted derivatives of 3-phenyl-4-cyanopyrroles, the compounds of this invention have a markedly enhanced fungicidal activity.

Surprisingly, it has been found that the compounds of formula I of this invention have, for practical purposes, a very useful biocidal activity spectrum against harmful microorganisms, in particular against phytopathogenic fungi and bacteria. Compounds of formula I have very advantageous curative, systemic and, in particular, preventive properties, and can be used for protecting numerous cultivated plants. With the compounds of formula I it is possible to inhibit or destroy the pests which occur in plants or in parts of plants (fruit, blossoms, leaves, stems, tubers, roots) in different crops of useful plants, while at the same time the parts of plants which grow later are also protected from attack by phytopathogenic microorganisms.

The compounds of formula I are effective for example against the phytopathogenic fungi belonging to the following classes: Ascomycetes, e.g. Erysiphe, Sclerotinia, Fusarium, Monilinia, Helminthosporium; Basidiomycetes, e.g. Puccinia, Tilletia, Rhizoctonia; as well as the Oomycetes belonging to the class of Phycomycetes, e.g. Phytophthora. As plant protective agents, the compounds of formula I can be used with particular success against important noxious fungi of the Fungi imperfecti family, e.g. against Cercospora, Pyricularia and, in particular, against Botrytis. Botrytis spp. (*B. cinerea, B. allii*) and the grey mould on vines, strawberries, apples, onions and other varieties of fruit and vegetables are a source of considerable economic damage. In particular, compound 1.1 of Table 1 has a broad activity spectrum. It exhibits an excellent fungicidal activity not only against Botrytis and Rhizoctonia, but is also suitable for successfully controlling Erysiphe and Venturia species. Furthermore, the compounds of formula I have a systemic action. In addition, compounds of formula I can be successfully used for protecting perishable goods of vegetable or animal origin. They control mould fungi such as Penicillium, Aspergillus, Rhizopus, Fusarium, Helminthosporium, Nigrospora and Alternaria, as well as bacteria such as butyric acid bacteria and yeast fungi such as Candida. Furthermore, these compounds have excellent activity against fungi which occur in seeds or in the soil.

As plant protective agents, the compounds of formula I have a very useful activity spectrum for practical application in agriculture for protecting cultivated plants, without damaging said plants by harmful side-effects.

The compounds of formula I can also be used as dressing agents for protecting seeds (fruit, tubers, grains) and plant cuttings against fungus infections and against phytopathogenic fungi which occur in the soil, for which utility they are especially effective as cereal dressing agents for controlling fungus organisms such as Fusarium, Helminthosporium and Tilletia species.

Accordingly, the invention also relates to microbicidal compositions and to the use of the compounds of formula I for controlling phytopathogenic microorganisms, in particular phytopathogenic fungi, and for the preventive treatment of plants and stored goods of vegetable or animal origin to protect them from infestation by such microorganisms.

Target crops to be protected within the scope of the present invention comprise e.g. the following species of plants: cereals (wheat, barley, rye, oats, rice, sorghum and related crops); beet (sugar beet and fodder beet); pomes, drupes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, marrows, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor); or plants such as maize, tobacco, nuts, coffee, sugar cane, tea, vines, hops, bananas and natural rubber plants, as well as ornamentals (composites).

For storage protection, the compounds of formula I are used in unmodified form or, preferably, together with the adjuvants conventionally employed in the art of formulation, and are therefore formulated in known manner to e.g. emulsifiable concentrates, brushable pastes, directly sprayable or dilutable solutions, dilute emulsions, wettable powders, soluble powders, dusts, granulates, and also encapsulations in e.g. polymer substances. The methods of application, such as spraying, atomising, dusting, scattering, coating or pouring, and the formulation of the composition, are chosen in accordance with the intended objectives and the prevailing circumstances. Suitable rates of application are in general in the range from 0.01 to not more than 2 kg of active ingredient per 100 kg of substrate to be protected. However, they depend very materially on the nature (surface area, consistency, moisture content) of the substrate and its environmental influences.

Within the scope of this invention, storable goods will be under stood as meaning natural substances of vegetable and/or animal origin and the products obtained therefrom by further processing, for example the plants listed below whose natural life cycle has been interrupted and the parts thereof (stalks, leaves, tubers, seeds, fruit, grains) which are in freshly harvested or further processed form (predried, moistened, crushed, ground, roasted). The following produce may be cited by way of example, without any restriction to the field of use within the scope of this invention: cereals (wheat, barley, rye, oats, rice, sorghum and related crops); beet (carrots, sugar beet and fodder beet); pomes, drupes and soft fruit (apples, pears, plums, peaches, almonds, cherries, strawberries, rasberries and blackberries); leguminous plants (beans, lentils, peas, soybeans); oil plants (rape, mustard, poppy, olives, sunflowers, coconuts, castor oil plants, cocoa beans, groundnuts); cucmber plants (cucumber, marrows, melons); fibre plants (cotton, flax, hemp, jute, ramie); citrus fruit; vegetables (spinach, lettuce, asparagus, cabbages, onions, tomatoes, potatoes, paprika); lauraceae (avocados, cinnamon, camphor), or maize, tobacco, nuts, coffee, sugar cane, tea, vines, chestnuts, hops, bananas, grass and hay.

A preferred method of applying the active ingredient comprises spraying or wetting the substrate with a liquid formulation, or mixing the substrate with a solid formulation, of the active ingredient. The invention also relates to the described method of preserving storable goods.

The compounds of formula I are normally applied in the form of compositions and can be applied to the crop area, plant or substrate to be treated, simultaneously or in succession, with further compounds. These compounds can be both fertilisers or micronutrient donors or other preparations that influence plant growth. They can also be selective herbicides, insecticides, fungicides, bactericides, nematicides, molluscicides or mixtures of several of these pesticides, if desired together with further carriers, surfactants or application promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers. Phospholipids are particularly useful adjuvants.

A preferred method of applying a compound of the formula I, or an (agro)chemical composition which contains at least one of said compounds, is foliar application. The number of applications and the rate of application depend on the risk of infestation by the corresponding pathogen (species of fungus). However, the compound of formula I can also penetrate the plant through the roots via the soil (systemic action) by impregnating the locus of the plant with a liquid formulation, or by applying the compounds in solid form to the soil, e.g. in granular form (soil application). The compounds of formula I may also be applied to seeds (coating) by impregnating the seeds either with a liquid formulation containing a compound of formula I, or coating them with a solid formulation. In special cases, further types of application are also possible, e.g. selective treatment of the plant stems or buds.

The compounds of formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Suitable rates of application are normally from 50 g to 5 kg of active ingredient (a.i.) per hectare, preferably from 100 g to 2 kg a.i./ha, most preferably from 200 g to 600 g a.i./ha.

The formulations, i.e. the compositions, preparations or mixtures containing the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil, sunflower oil or soybean oil; or water.

The solid carriers used e.g. for dusts and dispersible powders, are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition a great number of pregranulated materials of inorganic or organic nature can be used, e.g. especially dolomite or pulverised plant residues, e.g. cork powder or sawdust.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of ligninsulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphated adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylendiamino-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenol-polyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyl-trimethylammonium chloride or benzyl bis(2-chloroethyl)ethylammonium bromide. In the field of storage protection, the auxiliaries which are acceptable for human and animal nutrition are preferred.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also contain further auxiliaries such as stabilisers, antifoams, viscosity regulators, binders, tackifiers as well as fertilisers or other active ingredients for obtaining special effects.

Such (agro)chemical compositions constitute an object of the present invention.

The invention is illustrated by the following non-limitative Examples (percentages and parts are by weight).

1. PREPARATORY EXAMPLES:

1.1 Preparation of methyl 2-[3-(2,2-difluorobenzodioxol-4-yl)-4-cyanopyrrol-1-yl]acetate (intermediate)

To a solution of 15 g of 3-(2,2-difluorobenzodioxol-4-yl)-4-cyanopyrrole in 20 ml of dimethyl formamide are added 9.1 g of potassium carbonate. Then 6.1 ml of methyl bromoacetate are added dropwise at 20°–30° C. to the resultant suspension, and the reaction mixture is heated for 18 hours to 55° C. The reaction mixture is concentrated by evaporation on a rotary evaporator and the residue is partitioned between 100 ml of water and 100 ml of methylene chloride. The organic phase is separated and washed with a saturated solution of sodium chloride, dried over sodium sulfate, filtered, and the solvent is removed by evaporation, to give beige crystals of methyl 2-[3-(2,2-difluorobenzopioxol-4-yl)-4-cyanopyrrol-1-yl]acetate which melt at 138°–140° C.

1.2 Preparation of methyl 3-hydroxy-2-[3-(2,2-difluorobenzodioxol-4-yl)-4-cyanopyrrol-1-yl]acrylate To a solution of 3.14 g of methyl 2-[3-(2,2-difluorobenzodioxol-4-yl)-4-cyanopyrrol-1-yl]acetate in 40 ml of methyl formate are added 36 g of 80% sodium hydroxide at 5°–10° C. The reaction mixture is stirred overnight at room temperature, acidified with 1N hydrochloric acid, and extracted with ether. The ether extract is concentrated by evaporation and the crude mixture is chromatographed over silica gel with a 6:1 mixture of toluene/ethyl acetate, to give pale beige crystals which melt at 141°–143° C.

Compounds 2 to 15 listed in the Table are prepared in analogous manner.

1.3 Preparation of the sodium salt of methyl 3-hydroxy-2-[3-(2,2-difluorobenzodioxol-4-yl)-4-cyanopyrrol-1-yl]acrylate To a solution of 3.14 g of methyl 2-[3-(2,2-difluorobenzodioxol-4-yl)-4-cyanopyrrol-1-yl]acetate in 40 ml of methyl formate are added 0.36 g of 80% sodium hydride at 5°–10° C. The reaction mixture is stirred overnight at room temperature and filtered. The crystalline product is washed with ether and dried. The title compound melts higher than 210° C. (dec.).

TABLE 1

| Example | $R_1$ | $R_2$ | $R_3$ | m.p. |
|---|---|---|---|---|
| 1 | F,F-benzodioxol | | $CH_3$ | 141–143° C. |
| 2 | H | H | $CH_3$ | 120–140° C. |
| 3 | Cl | H | $CH_3$ | 122–123° C. |
| 4 | H | Cl | $CH_3$ | 122–130° C. |
| 5 | Cl | Cl | $CH_3$ | 153–155° C. |
| 6 | H | Br | $CH_3$ | 108–110° C. |
| 7 | H | $CF_3$ | $CH_3$ | 114–116° C. |
| 8 | H | $CF_3$ | $CH_3$ | |
| 9 | F,F-benzodioxol | | $C_2H_5$ | 105–107° C. |
| 10 | F,F-benzodioxol | | $n$-$C_6H_{13}$ | |
| 11 | F,F-benzodioxol | | $CH_2$-phenyl | |
| 12 | H | $NO_2$ | $CH_3$ | |
| 13 | H | $NO_2$ | $CH_3$ | |
| 14 | F,F-benzodioxol | | cyclohexyl | |

TABLE 1-continued

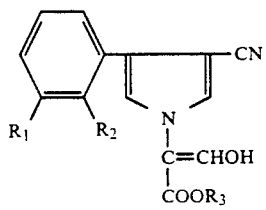

| Example | R₁ | R₂ | R₃ | m.p. |
|---|---|---|---|---|
| 15 | F | F | △ (cyclopropyl via C(F)(F) with two O) | |

2. FORMULATION EXAMPLES FOR LIQUID ACTIVE INGREDIENTS OF FORMULA I
(throughout, percentages are by weight)

| 2.1. Emulsifiable concentrates | (a) | (b) | (c) |
|---|---|---|---|
| a compound of Table 1 | 25% | 40% | 50% |
| calcium dodecylbenzenesulfonate | 5% | 8% | 6% |
| castor oil polyethylene glycol ether (36 mol of ethylene oxide) | 5% | — | — |
| tributylphenol polyethylene glycol ether (30 mol of ethylene oxide) | — | 12% | 4% |
| cyclohexanone | — | 15% | 20% |
| xylene mixture | 65% | 25% | 20% |

Emulsions of any required concentration can be produced from such concentrates by dilution with water.

| 2.2 Solutions | (a) | (b) | (c) | (d) |
|---|---|---|---|---|
| a compound of Table 1 | 80% | 10% | 5% | 95% |
| ethylene glycol monomethyl ether | 20% | — | — | — |
| polyethylene glycol (mol. wt. 400) | — | 70% | — | — |
| N-methyl-2-pyrrolidone | — | 20% | — | — |
| epoxidised coconut oil | — | — | 1% | 5% |
| petroleum distillate (boiling range 160–190° C.) | — | — | 94% | — |

These solutions are suitable for application in the form of micro-drops.

| 2.3. Granulates | (a) | (b) |
|---|---|---|
| a compound of Table 1 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off under vacuum.

| 2.4. Dusts | (a) | (b) |
|---|---|---|
| a compound of Table 1 | 2% | 5% |
| highly dispersed silicic acid | 1% | 5% |
| talcum | 97% | — |
| kaolin | — | 90% |

Ready-for-use dusts are obtained by intimately mixing the carriers with the active ingredient.

| 2.5. Wettable powders | (a) | (b) | (c) |
|---|---|---|---|
| a compound of Table 1 | 25% | 50% | 75% |
| sodium ligninsulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.6. Emulsifiable concentrate | |
|---|---|
| compound of Table 1 | 10% |
| octylphenol polyethlene glycol ether (4–5 mol of ethylene oxide) | 3% |
| calcium dodecylbenzenesulfonate | 3% |
| castor oil polyglycol ether (36 mol of ethylene oxide) | 4% |
| cyclohexanone | 30% |
| xylene mixture | 50% |

Emulsions of any required concentration can be obtained from this concentrate by dilution with water.

| 2.7. Dusts | (a) | (b) |
|---|---|---|
| a compound of Table 1 | 5% | 8% |
| talcum | 95% | — |
| kaolin | — | 92% |

Ready-for-use dusts are obtained by mixing the active ingredient with the carrier, and grinding the mixture in a suitable mill.

| 2.8. Extruder granulate | |
|---|---|
| a compound of Table 1 | 10% |
| sodium ligninsulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.9. Coated granulate | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| 2.10. Suspension concentrate | |
|---|---|
| of a compound of Table 1 | 40% |
| ethylene glycol | 10% |
| nonylphenol polyethylene glycol (15 moles of ethylene oxide) | 6% |
| sodium ligninsulfonate | 10% |

| 2.10. Suspension concentrate | |
|---|---|
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. BIOLOGICAL EXAMPLES

Example 3.1.: Residual-protective action against Venturia inaequalis on apple shoots Apple cuttings with ca. 5 developed leaves are sprayed with a spray mixture (0.02% of compound of Table 1) prepared from a wettable powder formulation according to one of the foregoing Examples. The plants are infected 24 hours later with a conidia suspension of the fungus. The plants are then incubated for 5 days at 90-100% relative humidity and stood in a greenhouse for a further 10 days at 20°-24° C. Evaluation of scab infestation is made 15 days after infection. Spray mixtures which contain one of the compounds of the Table (e.g. compound 1 or 5) markedly inhibited fungus infestation.

Example 3.2.: Action against Botrytis cinerea on beans

Residual protective action

Bean plants ca. 10 cm in height are sprayed with a spray mixture (0.02% active ingredient) prepared from a wettable powder formulation of the test compound. After 48 hours the treated plants are infected with a conidia suspension of the fungus. The infected plants are incubated for 3 days at 95-100% relative humidity and 21° C. and then evaluated for fungus attack. The compounds of Table 1 inhibited the fungus infection very strongly in many cases. At a concentration of 0.02%, compounds 1 or 5 were fully effective (0 to 5% infestation). Fungus infestation was 100% on untreated and infected bean plants.

Example 3.3.: Action against Botrytis cinerea on apples

Artificially damaged apples are treated by dropping a spray mixture (concentration: 6 ppm) prepared from a wettable powder formulation of the test compound onto the injury sites. The treated fruit is then inoculated with a spore suspension of *Botrytis cinerea* and incubated for 1 week at high humidity and about 20° C. Evaluation is made by counting the number of injury sites attacked by rot and deducing the fungicidal action of the test compound therefrom. Compounds of Table 1 were very effective against Botrytis attack on apples. Compared with untreated controls (100% infestation), compounds 1 and 5 inhibited fungus attack almost completely.

Example 3.4.: Action against Alternaria solani on tomatoes

After a cultivation period of 3 weeks, tomato plants are sprayed with a spray mixture (0.06% active ingredient) prepared from a wettable powder formulation of the test compound. After 24 hours the tomato plants are treated with a conidia suspension of the fungus. Evaluation of fungicidal action is made on the basis of fungus infestation after the plants have been incubated for 8 days at high humidity and a temperature of 18°-22° C. Compounds of Table 1 reduced Alternaria attack substantially; thus compound 1 inhibited attack completely (0 to 5%).

Example 3.5.: Action against Pyricularia oryzae on rice plants

After a cultivation period of 2 weeks, rice plants are sprayed with a spray mixture (0.02% active ingredient) prepared from a wettable powder formulation of the test compound. After 48 hours the treated plants are infected with a conidia suspension of the fungus. Evaluation of fungus attack is made after incubation for 5 days at 95-100% relative humidity and 24° C.

Compounds of Table 1 inhibited Pyricularia attack effectively. Thus, for example, compound 1 reduced attack to less than 10%.

Example 3.6: Action against Rhizoctonia solani (soil fungus) on rice plants

Protective local leaf application 12-day-old rice plants are sprayed with a spray mixture (200 and 60 ppm) prepared from a formulation of the test compound. One day later the treated plants are infected with a suspension of mycelium and sclerotia of R. solani. After incubation for 6 days at 27° C. (by day) and 23° C. (by night) and 100% relative humidity (humidity box) in a climatic chamber, evaluation of fungus infestation on the leaf sheath, leaves and stem is made.

Compounds of the Tables exhibit good activity by inhibiting Rhizoctonia attack. On the other hand, attack was 100% on untreated and infected control plants. Compound 1 inhibits fungus attack to 0 to 5%, and compound 5 to 5-20%.

What is claimed is:

1. A compound of formula I

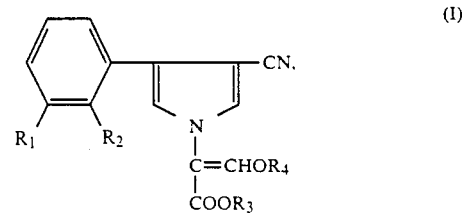

wherein
R$_1$ and R$_2$ are each independently of the other unsubstituted or halogen-substituted C$_1$-C$_8$alkyl, halogen, nitro or hydrogen, or R$_1$ and R$_2$, when taken together, are —OCF$_2$O,
R$_3$ is C$_1$-C$_8$alkyl, cycloalkyl or benzyl, and
R$_4$ is hydrogen or an alkali metal or alkaline earth metal.

2. A compound of formula I according to claim 1, wherein R$_4$ is hydrogen.

3. A compound of formula I according to claim 2, wherein R$_1$ and R$_2$ are each independently of the other unsubstituted or halogen-substituted C$_1$-C$_8$alkyl, halogen, nitro or hydrogen, or R$_1$ and R$_2$, when taken together, are —OCF$_2$O, and R$_3$ is C$_1$-C$_8$alkyl or benzyl.

4. A compound according to claim 3, wherein R$_1$ and R$_2$ are each independently of the other methyl, trifluoromethyl, chloro, bromo or hydrogen, or or R$_1$ and R$_2$, when taken together, are —OCF$_2$O, and R$_3$ is methyl, ethyl, n-hexyl or benzyl.

5. A compound according to claim 4, wherein $R_3$ is methyl or ethyl.

6. Methyl 2-[3-(2,2-difluorobenzodioxol-4-yl)-4-cyanopyrrol-1-yl]-3-hydroxyacrylate according to claim 5.

7. Methyl 2-[3-(2,3-dichlorophenyl)-4-cyanopyrrol-1-yl]-3-hydroxyacrylate according to claim 5.

8. A microbicidal composition for controlling microorganisms or for protecting living plants from attack by said microorganisms and/or for preserving perishable storable goods of vegetable or animal origin, which composition contains as active component at least one compound as defined in claim 1 together with a suitable carrier.

9. A method of controlling phytopathogenic microorganisms or of protecting cultivated plants from attack by said microorganisms, which method comprises applying to said plants, to parts of plants or to the locus thereof a compound of formula I according to claim 1.

10. A method of dressing seeds and plant cuttings to afford protection against attack by fungus organisms, which method comprises applying to said seeds or plant cuttings a compound of formula I according to claim 1.

11. A method of preserving storable goods of vegetable and/or animal origin or of protecting said goods from attack by harmful microorganisms, which method comprises treating said goods with a microbicidally effective amount of a compound of formula I according to claim 1.

* * * * *